US009129119B2

(12) United States Patent
Burke et al.

(10) Patent No.: US 9,129,119 B2
(45) Date of Patent: *Sep. 8, 2015

(54) ENFORCEMENT OF DATA PRIVACY TO MAINTAIN OBFUSCATION OF CERTAIN DATA

(71) Applicant: International Business Machines Corporation, Armonk, NY (US)

(72) Inventors: Michael George Burke, Yonkers, NY (US); Igor Peshansky, Hillsdale, NJ (US); Marco Pistoia, Amawalk, NY (US); Omer Tripp, Har-Adar (IL)

(73) Assignee: International Business Machines Corporation, Armonk, NY (US)

( * ) Notice: Subject to any disclaimer, the term of this patent is extended or adjusted under 35 U.S.C. 154(b) by 202 days.

This patent is subject to a terminal disclaimer.

(21) Appl. No.: 13/968,478

(22) Filed: Aug. 16, 2013

(65) Prior Publication Data
US 2013/0332990 A1 Dec. 12, 2013

Related U.S. Application Data

(63) Continuation of application No. 12/776,465, filed on May 10, 2010, now Pat. No. 8,544,104.

(51) Int. Cl.
*G06F 21/00* (2013.01)
*G06F 21/60* (2013.01)
*G06F 21/62* (2013.01)
*G06F 19/00* (2011.01)

(52) U.S. Cl.
CPC .............. *G06F 21/60* (2013.01); *G06F 19/322* (2013.01); *G06F 21/6245* (2013.01)

(58) Field of Classification Search
CPC .... G06F 21/60; G06F 21/6245; G06F 19/322
See application file for complete search history.

(56) References Cited

U.S. PATENT DOCUMENTS

| 8,276,206 | B2 | 9/2012 | LaRocca et al. |
| 2002/0169793 | A1* | 11/2002 | Sweeney .................... 707/204 |
| 2004/0199781 | A1 | 10/2004 | Erickson et al. |
| 2010/0154065 | A1 | 6/2010 | Cohen et al. |
| 2011/0119661 | A1 | 5/2011 | Agrawal et al. |
| 2011/0258206 | A1 | 10/2011 | El Emam et al. |
| 2011/0277037 | A1 | 11/2011 | Burke et al. |

OTHER PUBLICATIONS

L. Andersen. Jdbc 4.0 speciication, Sun Microsystems, Inc., 2006 (226 pages).

(Continued)

*Primary Examiner* — Brandon Hoffman
*Assistant Examiner* — Thong Truong
(74) *Attorney, Agent, or Firm* — Harrington & Smith; Louis J. Percello

(57) ABSTRACT

A computer-readable medium is disclosed that tangibly embodies a program of machine-readable instructions executable by a digital processing apparatus to perform operations including determining whether data to be released from a database is associated with one or more confidential mappings between sets of data in the database. The operations also include, in response to the data being associated with the one or more confidential mappings, determining whether release of the data meets one or more predetermined anonymity requirements of an anonymity policy. Methods and apparatus are also disclosed.

14 Claims, 18 Drawing Sheets

(56) References Cited

OTHER PUBLICATIONS

D. Elliott Bell and Leonard J. LaPadula. Secure computer systems: Mathematical foundations. Technical Report 2547, vol. I, Mitre, 1973. (42 pages).

Michael Burke, Igor Peshansy, Mukund Raghavachari, and Christoph Reichen-bach. Analysis of imperative xml programs. In DBPL 2007 • 11th international Symposium on Database Programming Languages, 2007. (15 pages).

Valentina Ciriani, Sabrina De Capitani di Vimercati, Sara Foresti, and Pierangela Samarati. k-anonymity. In Secure Data Management in Decentralized Systems, vol. 33, pp. 323-353. Springer, 2007. (36 pages).

A. Machanavajjhala, J. Gehrke, and D. Kifer. 1-diversity: Privacy beyond k-anonymity. In ICDE 2006: Proceedings of the International Conference on Data Engineering, 2006. (12 pages).

Samarati P. and Sweeney L. Protecting privacy when disclosing information: k-anonymity and its enforcement through generalization and suppression. Technical Report SRI-CSL-98-04. SRI Computer Science Laboratory, 1998. (19 pages).

Manu Sridharan, Stephen J. Fink, and Rastislav Bodik. Thin slicing. In PLDI 2007: Proceedings of the ACM SIGPLAN 2007 Conference on Programming Language Design and Implementation, pp. 112-122, 2007. (11 pages).

Frank Tip. A survey of program slicing techniques. Journal of Programming Languages, 3(3):121-189, 1995. (65 pages).

Omer Tripp, Marco Pistoia, Stephen J. Fin anu Sridharan, and Omri Weisman. Taj: Efective taint analysis for in PLDL 2009: Proceedings of the ACM SIGPLAN 2009 Conference on Programming Language Design and Implementation 2009 (11 pages).

"k-Anonymity: A Model for Protecting Privacy", Latanya Sweeney, International Journal on Uncertainty, Fuzziness and Knowledge-based Systems, May 2002, 14 pgs.

V. Ciriani et al., "k-Anonymity", Springer US Advances in Information Security (2007), http://springerlink.com/content/ht1571nI63563x16/full.txt.pdf, 36 pages.

M. Burke et al., IBM Reaserach Report, "Impact of Object-Oriented Source Code with Respect to Database Schema Changes", Dec. 3, 2008 Computer Science, 27 pages.

\* cited by examiner

200

| | | | Q | | |
|---|---|---|---|---|---|
| Name | Race | Birth date | Gender | ZIP | Problem |
| John Doe | Black | 01/01/1965 | M | 02141 | Short breath |
| James Rossi | Black | 02/02/1965 | M | 02142 | Chest pain |
| Alice Smith | Black | 03/03/1965 | F | 02131 | AIDS |
| Joanna Rice | Black | 04/04/1965 | F | 02132 | Cancer |
| Mark Cohen | White | 03/03/1964 | M | 02135 | Chest pain |
| Paul Smith | White | 04/04/1964 | M | 02136 | Obesity |
| Luke Rossi | White | 05/05/1964 | M | 02137 | Short breath |
| Michael Ross | White | 01/01/1967 | M | 02138 | Chest pain |
| Thomas Thomson | White | 02/02/1967 | M | 02139 | Obesity |

| Name | Race | Birth date | Gender | ZIP | Telephone |
|---|---|---|---|---|---|
| John Doe | Black | 01/01/1965 | M | 02141 | 123-456-7890 |
| James Rossi | Black | 02/02/1965 | M | 02142 | 098-765-4321 |
| Alice Smith | Black | 03/03/1965 | F | 02131 | 321-654-0987 |
| Joanna Rice | Black | 04/04/1965 | F | 02132 | 135-246-7890 |
| Mark Cohen | White | 03/03/1964 | M | 02135 | 111-222-3456 |
| Paul Smith | White | 04/04/1964 | M | 02136 | 444-555-6789 |
| Luke Rossi | White | 05/05/1964 | M | 02137 | 333-444-5678 |
| Michael Ross | White | 01/01/1967 | M | 02138 | 777-888-1234 |
| Thomas Thomson | White | 02/02/1967 | M | 02139 | 123-456-0987 |

| Name | Race | Birth date | Gender | ZIP | Problem |
|---|---|---|---|---|---|
| * | Black | //1965 | M | 0214* | Short breath |
| * | Black | //1965 | M | 0214* | Chest pain |
| * | Black | //1965 | F | 0213* | AIDS |
| * | Black | //1965 | F | 0213* | Lung cancer |
| * | White | //1964 | M | 0213* | Chest pain |
| * | White | //1964 | M | 0213* | Obesity |
| * | White | //1964 | M | 0213* | Short breath |
| * | White | //1967 | M | 0213* | Chest pain |
| * | White | //1967 | M | 0213* | Obesity |

2 indistinguishable entries — 510-1
2 indistinguishable entries ⟹ 2-anonymity — 510-2
3 indistinguishable entries — 510-3
2 indistinguishable entries — 510-4

FIG. 5

| Name | Race | Birth date | Gender | ZIP | Problem |
|---|---|---|---|---|---|
| * | Black | //1965 | M | 0214* | Short breath |
| * | Black | //1965 | M | 0214* | Chest pain |
| * | Black | //1965 | F | 0213* | Lung cancer |
| * | Black | //1965 | F | 0213* | Lung Cancer |
| * | White | //1964 | M | 0213* | Chest pain |
| * | White | //1964 | M | 0213* | Obesity |
| * | White | //1964 | M | 0213* | Short breath |
| * | White | //1967 | M | 0213* | Chest pain |
| * | White | //1967 | M | 0213* | Obesity |

- 2 indistinguishable entries (510-1)
- 2 indistinguishable entries ⟹ 1-anonymity (510-2)
- 3 indistinguishable entries (510-3)
- 2 indistinguishable entries (510-4)

FIG. 6

```
conn = SampleUtil.getConnection (args[0], args[1], args[2]);
Data db = zero.data.runtime.factory.DataFactory.getData (conn);

// Extract SALARY column
Iterator<Table> getEmployees = db.queryIterator(
    "select SALARY from TABLE", Table.class);

// iterate thru employee rows in TABLE, summing up the total salary for
// a department
double dept_salary = 0.00;
while (getEmployees.hasNext() ) {
    Table employee = getEmployees.next();
    // retrieves and add the employee's salary
    dept_salary = dept_salary + table.getSalary();
}
// allowed due to declassification policy if getEmployees has size > k
System.out.println(dept_salary);
```

Release point & possible breakage of *k*-anonymity-- should be preceded by a cardinality check

FIG. 10

```
// iterate thru employee rows in TABLE, summing
// up the total salary for a department
...
// allowed due to declassification policy if getEmployees has size > k
System.out.println(dept_salary);  // ← Release point & possible breakage of k-anonymity--should be preceded by a cardinality check // add new employees record(s) to TABLE
System.out.println(empl_name + " added"); // cannot print empl_salary  ← Release point, no confidential data or mapping is being revealed // iterate thru employee rows in TABLE, summing up the new total salary for
// the department
...
// allowed only if the set of new employees has cardinality > k
System.out.println(dept_newsalary - dept_salary);  ← Release point & possible breakage of k-anonymity--should be preceded by a cardinality check
```

FIG. 11

| Table - BOOKSTORE | | | | |
|---|---|---|---|---|
| Schema | :PISTOIA | | | |
| Creator | :CENTONZR | | | |
| Columns | :5 | | | |

Columns

| Key | Name | Data type | Length | Nullable |
|---|---|---|---|---|
| | USERNAME | CHARACTER | 10 | Yes |
| | GENDER | CHARACTER | 10 | Yes |
| | ZIPCODE | BIGINT | 8 | Yes |
| | AGE | INTEGER | 4 | Yes |
| | BOOKS | CHARACTER | 30 | Yes |

Actions:
- Open
- Query
- Show Related Objects
- Create New Table

FIG. 12

| USERNAME | GENDER | ZIPCODE | AGE | BOOKS | |
|---|---|---|---|---|---|
| Linda | F | 10523 | 30 | ABC | ... |
| Marc | M | 10501 | 34 | ABC | ... |
| Marc | M | 10501 | 34 | XYZ | ... |
| Mike | M | 10532 | 44 | ABC | ... |
| Mike | M | 10532 | 44 | HJK | ... |
| Mary | F | 10598 | 50 | XYZ | ... |
| John | M | 10532 | 41 | ABC | ... |
| Linda | F | 10523 | 30 | XYZ | ... |
| Marc | M | 10501 | 34 | HJK | ... |
| Paul | M | 10501 | 32 | ABC | ... |
| Richard | M | 10501 | 33 | ABC | ... |
| Paul | M | 10501 | 32 | XYZ | ... |
| Richard | M | 10501 | 33 | XYZ | ... |
| Robert | M | 10532 | 43 | ABC | ... |
| Robert | M | 10532 | 43 | HJK | ... |

FIG. 13

```
ResultSet rs = statement.executeQuery (
    "SELECT USERNAME, BOOKS FROM DB.BOOKSTORE WHERE BOOKS = 'ABC' ");
ResultSetMetaData rsmd = rs.getMetaData ();
Set<String> users = new HashSet<String> ();
while (rs.next () ) {
    String userName = rs.getString(1) ;
    users.add (userName);
}
```

FIG. 14A

| USERNAME | BOOKS |   |
|----------|-------|---|
| Linda    | ABC   | ... |
| Marc     | ABC   | ... |
| Mike     | ABC   | ... |
| John     | ABC   | ... |
| Paul     | ABC   | ... |
| Richard  | ABC   | ... |
| Robert   | ABC   | ... |

FIG. 14B

```
• ResultSet rs = statement.executeQuery (
    "SELECT USERNAME, BOOKS FROM DB.BOOKSTORE WHERE BOOKS = 'ABC' ");
  ResultSetMetaData rsmd = rs.getMetaData ();
  Set<String> users = new HashSet<String> ();
  while (rs.next ()) {
    String userName = rs.getString(1);
    users.add (userName);
  }
```

SELECT USERNAME, BOOKS, BOOKS FROM DB.BOOKSTORE WHERE BOOKS = 'ABC' AND AGE BETWEEN 30 AND 35 AND GENDER = 'M' AND ZIPCODE = 10501

FIG. 15A

```
SELECT USERNAME, BOOKS FROM DB.BOOKSTORE WHERE BOOKS = 'ABC'
AND AGE BETWEEN 30 AND 35 AND GENDER = 'F' AND ZIPCODE = 10501
```

```
• ResultSet rs = statement.executeQuery (
    "SELECT USERNAME, BOOKS FROM DB.BOOKSTORE WHERE BOOKS = 'ABC' ");
  ResultSetMetaData rsmd = rs.getMetaData ();
  Set<String> users = new HashSet<String> ();
  while (rs.next () ) {
      String userName = rs.getString(1);
      users.add (userName);
  }
```

FIG. 16A

| Books Other than ABC | Quantity |
|---|---|
| XYZ | ✓ |
| HUK | |
| DEF | |
| LMN | |
| PQR | |

Release point & possible breakage of k-anonymity-- should be preceded by a cardinality check:

users.size () > k

"Age range" and "area" can be inferred by running multiple queries

Other female users in your age range and in your area who bought book ABC also bought book XYZ

FIG. 16B

ENFORCEMENT OF DATA PRIVACY TO MAINTAIN OBFUSCATION OF CERTAIN DATA

CROSS-REFERENCE TO RELATED APPLICATIONS

This application is a continuation of Ser. No. 12/776,465, filed on May 10, 2010, the disclosure of which is hereby incorporated by reference in its entirety.

BACKGROUND

This invention relates generally to data privacy and, more specifically, relates to enforcing data privacy to maintain obfuscation of certain data.

In the information-security field, it is widely regarded that there are dimensions of information security: (1) Integrity, which means that valuable information should not be damaged by any computation and that security-sensitive computations should not be influenced by untrusted values; and (2) Confidentiality, which means that it is ensured that information is accessible only to those authorized to have access.

A typical information-flow-security model is as follows: Data and principals are associated with labels that determine which principals have access to which data. These labels form a lattice, in which elements are partially ordered. In this partial order, the terms "high" and "low" take different meanings depending on the security dimension they represent. Specifically, in integrity, "high" means "untrusted" and "low" "trusted"; in confidentiality, "high" means "secret" and "Low" "public".

In terms of information flow, the rule is that there should be no flow of information from high to low. However, an information policy can "downgrade" data and principals. High-to-low information flow is allowed as long as the high in information has been sufficiently downgraded. In integrity, "downgrading" means "endorsing"; in confidentiality, it means "declassifying".

Thus, certain parts of secret information can be declassified and revealed to certain public listeners. For instance, the last 4 digits of a social security number (SSN) can be revealed to a bank teller. Another example is the following. Assume that the passwords of a set of users are secretly stored in a file. When a user attempts to log in by entering a user ID and password pair, the authentication system has to check that the password entered is correct. To do so, it has to verify that the password stored in the set of passwords for that particular user ID matches the password that was entered. If a match is found, then the authentication system returns a success message to the user and allows the user to log in. If no match is found, the authentication system returns an error message to the user. Regardless of whether the message returned is a success message or an error message, the message itself must be considered "high" because it is obtained as a result of comparing the password that was entered by the user with the passwords in the password file. Therefore, displaying that message to the user should be considered an information-flow-security violation. Theoretically, a user could use the information in the message to try different passwords until the correct one is identified (a "dictionary attack"). According to the information-flow-security principle, then, an authentication mechanism violates information-flow security. However, assuming that the authentication system allows only a limited number of attempts (for example, three) before locking the account, the message returned to the user can be considered declassified. Furthermore, certain parts of untrusted input can be endorsed and used in certain trusted computations. For instance, untrusted user input can be used in a Web application if the input is properly formatted and is verified to not contain substrings that could compromise the integrity of the system.

Private data stored, e.g., in databases is therefore sometimes declassified and then released. An issue with release is whether, even after declassification and/or endorsement, the release still maintains privacy for those people whose data is in the databases. This is particularly true when information from releases from multiple databases can be combined by an entity (e.g., an attacker) to determine private information about a person who has data in both databases.

SUMMARY

In an exemplary embodiment, a computer-readable medium is disclosed that tangibly embodies a program of machine-readable instructions executable by a digital processing apparatus to perform operations including determining whether data to be released from a database is associated with one or more confidential mappings between sets of data in the database. The operations also include, in response to the data being associated with the one or more confidential mappings, determining whether release of the data meets one or more predetermined anonymity requirements of an anonymity policy.

In another exemplary embodiment, an apparatus is disclosed that includes one or more processors and one or more memories including instructions. The one or more processors are configured, in response to executing the instructions, to cause the apparatus to perform at least the following: determining whether data to be released from a database is associated with one or more one confidential mappings between sets of data in the database. The one or more processors are also configured, in response to the data being associated with the one or more confidential mapping, determining whether release of the data meets at least one predetermined anonymity requirement of an anonymity policy.

In another exemplary embodiment, a method is disclosed that includes determining whether data to be released from a database is associated with one or more confidential mappings between sets of data in the database. The method also includes, in response to the data being associated with the one or more confidential mappings, determining whether release of the data meets one or more predetermined anonymity requirements of an anonymity policy.

BRIEF DESCRIPTION OF THE SEVERAL VIEWS OF THE DRAWINGS

The foregoing and other aspects of embodiments of this invention are made more evident in the following Detailed Description of Exemplary Embodiments, when read in conjunction with the attached Drawing Figures, wherein:

FIG. 3 shows the private medical data table of FIG. 2 and illustrates a quasi identifier, Q;

FIG. 4 shows an exemplary public voting database table;

FIG. 5 shows an example of released data in table form that is obfuscated correctly to meet 2-anonymity;

FIG. 6 shows an example of the table in FIG. 5, with a minor change illustrating data insufficiently obfuscated such that 2-anonymity is not met;

FIG. 10 shows an example of program code that retrieves, through a database query, information from an employee database and potentially does not maintain proper obfuscation of employee salaries for release of the information;

FIG. 11 shows ail example of program code that retrieves, through database queries, certain information from an employee database and releases the information at release points, and whether those release points could release data that maintains obfuscation;

FIG. 12 is an example of an entry used for a bookstore;

FIG. 13 is an example of a table of entries for purchases made at the bookstore;

FIG. 14A is an example of program code that queries the bookstore database to determine which users purchased book ABC;

FIG. 14B is a list output by the program code of the users who bought book ABC;

FIG. 15A shows the program code of FIG. 14A modified for a more specific query of what other male users in a certain age range and in a certain area who bought book ABC also bought book XYZ;

FIG. 16A shows the program code of FIG. 14A modified for a more specific query of what other female users in a certain age range and in a certain area who bought book ABC also bought book XYZ;

FIG. 16B shows results of the query of what other female users in a certain, age range and in a certain area who bought book ABC also bought book XYZ, how release of this data does not maintain obfuscation, and how multiple attacks can be used to reveal private information.

DETAILED DESCRIPTION

An exemplary context for the invention is information security for multi-tier applications. In these applications, a client is a database application or a browser, and a server is a database or a Web site. Security vulnerabilities are addressed that arise when confidential data is declassified. For example, private medical data is released in obfuscated form for epidemiological studies, and private personal data is released in obfuscated form in the publication of online-store sales statistics. Also, confidential data is sometimes declassified when aggregated. For example, where the salary of an individual is confidential, the total salary of a department may be released if the department is sufficiently large.

Security vulnerabilities can arise due to these declassifications. Attackers can combine obfuscated data with other obfuscated data and/or public data to infer confidential data. In a medical database table, an entity is identified by the name of the patient, and another column records a medical problem of the patient, which is sensitive data. In this case, the linking of information between an entity and sensitive data associated with that entity can be classified as confidential. This form of confidentiality is known as "anonymity."

Attackers can also infer confidential data from an aggregation, if the aggregated data is insufficiently large. Attackers can further infer confidential data through comparisons of multiple aggregations that differ by small variations. Thus, such attackers can use a variety of attacks to infer confidential data from publicly released information that was thought to be declassified.

The attacks can be separated into "active" and "passive" attacks. An active attack occurs when a programmer either maliciously or inadvertently writes out a value that would allow inferring confidential data. A passive attack occurs where the attacker infers confidential data without write access to the application code.

Methods, apparatus, and program products are disclosed below, some based on static analysis, to protect against the inference of confidential data from declassified information through active and passive attacks. In particular, focus is placed on the protection of data that is private due to anonymity requirements. Certain exemplary embodiments below include:

1) Formulation of an information flow security model for anonymity, as an instance of an information flow model for confidentiality that specifies confidential mappings;

2) Static-enforcement mechanisms for enforcing such anonymity policies (where "static" means that these mechanisms do not execute the code but just analyze it); and 3) An observation that a cardinality check is sufficient to enforce k-anonymity for aggregated data.

Figures 1, 2:
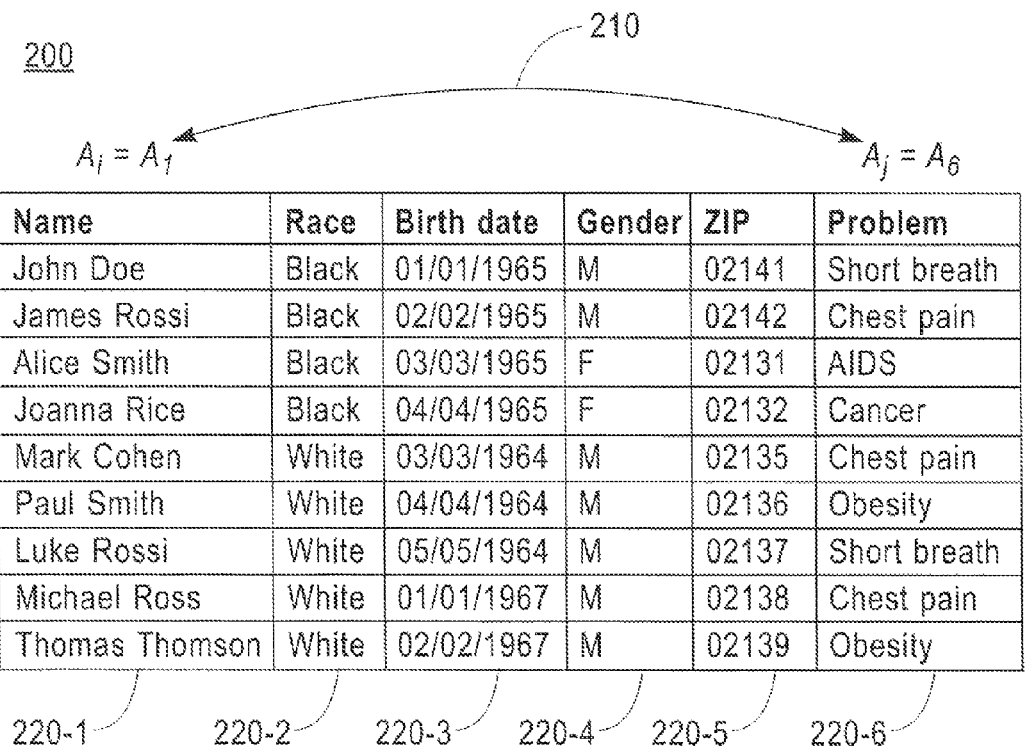
FIG. 1 shows a table illustrating how downgrading corresponds to anonymization.
FIG. 2 shows an exemplary private medical database table also illustrating a confidential mapping.

Now that an introduction has been given, a more detailed description is given. First, some additional concepts related to integrity and confidentiality (refer to the discussion above) are described. Turning to FIG. 1, a table illustrating, e.g., how downgrading corresponds to anonymization. Anonymity (as shown in the Privacy column) is a form of confidentiality. The private data is a link between an entity and some data associated with that entity. When the dimension of information-flow security is privacy, downgrading corresponds to anonymization. Thus, when it comes to privacy, information-flow security requires that there is not flow that goes from private (corresponding to "high") to public (corresponding to "low"); the process of downgrading is called "anonymization".

Data extracted from a database can be anonymized to protect confidential links. Even after anonymization, the released information can still be sufficient to reveal a confidential link, when combined with other anonymized data and/or public data. One possible solution for this is an anonymity policy that requires a level k of anonymity, where each entity in the release is indistinguishable from at least k−1 other entities. For k large enough, this should improve security, as it makes it less likely that released information, even if combined with other information, will reveal private information.

Among the techniques proposed herein for providing anonymity in the release of private data, the k-anonymity approach focuses on two techniques in particular: "generalization" and "suppression," which, unlike other existing techniques, such as scrambling or swapping, preserve the truthfulness of the information.

Generalization consists in substituting the values of a given column with more general values. To this purpose, the notion of domain (i.e., the set of values that the entries of a column can assume) is extended by assuming the existence of a generalized domain. A generalized domain contains generalized values and there exists a mapping between each domain and its generalization. For instance, ZIP codes can be generalized by dropping, at each generalization step, the least significant digit; postal addresses can be generalized to the street dropping the number), then to the city, to the county, to the state, and so on.

In the case of anonymity, the private data is in fact a private mapping: the link between an entity and some data associated with that entity. The mapping is defined herein as a "confidential mapping." FIG. 2 shows an exemplary private medical database table 200 also illustrating a confidential mapping 210. With the confidential mapping 210, columns 220 (220-1 through 220-6 in this example) of the database table 200 with confidential data are distinguished from a confidential association of the information in two columns. Sensitive information in a column 220 of the database table T (table 200) is not necessarily confidential. But the mapping of an identity of an entity to the corresponding value in a sensitive column can be classified as confidential. Thus, the confidential mapping 210 is used to map the name of an entity in column 220-1 to a problem experienced by the entity in column 220-6.

In this medical database table 200, an entity is identified by the patient's name, given in the Name column 220-1. The Problem column 220-6 records the medical problem of a patient. As previously described, neither column by itself contains confidential information, but the mapping of an entry in the Name column 220-1 to his/her medical problem (in column 220-6) can be classified as confidential, as shown in FIG. 2.

Exemplary embodiments of the invention augment a typical information flow security model with confidential mappings 210 that specify at least part of an anonymity policy. This extension is more formally described below.

Above, generalization was defined as the substitution of the values of a given column with more general values, where there exists a mapping between a domain for column values and the generalization of that domain. A mapping of a set of values into a generalized set forms a partitioning of the values into equivalence classes, where the members of an equivalence class all map into the same generalized value. This partitioning is referred to as obfuscation.

Turning now to FIGS. 2-5, FIG. 3 shows the private medical data table of FIG. 2 and illustrates a quasi identifier, Q. FIG. 4 shows an exemplary public voting database table 300 (including columns 320-1 through 320-6). FIG. 5 shows an example of released data in table form (table 500) that is obfuscated correctly to meet 2-anonymity. The medical database table 200 of FIG. 2 contains a confidential mapping 210 of an entry in the Name column to that entry's medical problem. This information is released in obfuscated form in table 500 of FIG. 5. The obfuscation of the information in a column is a partitioning of its data into column-specific equivalence classes. In table 500 of FIG. 5, birth date values are mapped into year of birth values, and zip code values are mapped into the values of the first four zip code digits.

When the information in table 500 of FIG. 5 is combined with that of a public voting system database table (FIG. 4), inferences can be made related to the confidential mapping 210.

The "quasi identifier" Q (shown in FIG. 3) is the set of columns 220, other than the column of sensitive data, that are included in an obfuscated release of the information in a private table. Q therefore includes columns 220-2 through 220-5 in this example. A formal definition is provided below. With respect to the information in Q, FIG. 5 shows four sets 510-1 through 510-4 of indistinguishable entries. One of these sets (set 520-2) includes the third and fourth rows.

Combined with the third and fourth rows of Table 300 of FIG. 4, one can infer that Alice Smith (and Joanna Rice) either has AIDS or lung cancer. The degree of anonymity of a table of obfuscated information can be measured by the size of the smallest set of indistinguishable entities. Where this size is k, the table is said to be k-anonymous. The table 500 shown in FIG. 5 is 2-anonymous. That is the reason why one can infer that Alice Smith (and Joanna Rice) either has AIDS or lung cancer, as observed above. The actual disease is not precisely known. This is consistent with the fact that the level of anonymity in this example is k=2. By imposing a higher level of anonymity (k>2), inferring the disease of a person in the set becomes increasingly more difficult.

The definition of k-anonymous can be refitted by the observation that where the information in the column (220-6) of sensitive data is identical among indistinguishable entities, one can infer more specific sensitive information from among those entities. A set of entities with the same quasi identifier value is said to be l-diverse if the set contains at least l different values for the sensitive column. For example, suppose that Joanna Rice also has lung cancer. Then the same obfuscation that resulted in Table 500 of FIG. 5 now results in Table 600 of FIG. 6, and one can infer that both Alice Smith and Joanna Rice have lung cancer. Given a refinement of the definition that takes l-diversity into account, Table 600 is 1-anonymous. Unfortunately, 1-anonymity means no anonymity at all, and that is why in the case in which Joanna Rice also has lung cancer, the disease of both Joanna Rice and Alice Smith is now completely known.

A formal definition of k-anonymity, which incorporates l-diversity and a formulation of obfuscation, is now presented.

Given a population of entities U, an entity-specific table $T(A_1, A_2, \ldots, A_n)$ where $C=\{A_1, \ldots, A_n\}$ is a set of columns with confidential mapping $(A_i, A_j)$ (e.g., confidential mapping 220), a subset Q of $\{A_1, \ldots, A_n\}\backslash A_i, A_j$ is a quasi identifier if there exist:

Two functions $f_1: U \rightarrow T$, $f_2: T \rightarrow U'$ such that $U \subseteq U'$ (T viewed as a set of records and U' offers a complete coverage of entities); and An entity $p \in U$ such that $f_2([f_1(p)]_Q)=\{p\}$, where the $[r]_Q$ indicates the equivalence class of record r modulo Q. This means that all the records in $[r]_Q$ are indistinguishable from each other when only the columns in Q are considered. Whether or not Q is a quasi identifier depends on the data in the database.

An obfuscated release R of the data in T is $T'(B_1, B_2, \ldots, B_n)$, where $B_1=A_1/\sim_1$, $B_2=A_2/\sim_2$, ..., $B_n=A_n/\sim_n$ and $\sim_1, \sim_2, \ldots, \sim_n$ are column-specific equivalence relations. Note: The confidential column may or may not be obfuscated.

An obfuscated release R provides k-anonymity with respect to a quasi identifier Q, where $k \in N$, if and only if for each record $p_1 \in R$, $\exists p_2, \ldots, p_k \in R | \forall m,n \in \{1, 2, \ldots, k\}$, $m \neq \Rightarrow p_m \neq p_n \wedge [p_m]_Q = [p_n]_Q \wedge [p_m]_{Aj} \neq [p_n]_{Aj}$ In other words, for each record $p_1$, there exist k−1 other records $p_2, \ldots, p_k$ all different from each other, such as these records are indistinguishable from each other when only the columns of Q are considered, but they are distinguishable from each other when only the values in column $A_j$ are considered (where $A_j$ is the column mapped to the identity column $A_i$ by the confidentiality mapping).

An information-flow anonymity policy specification is now formally defined as the following.

Let $(L, \cap, \cup)$ be a lattice of information-flow levels and an entity-specific table $T(A_1, \ldots, A_n)$, where $C=A_1, \ldots, A_n$ is the set of columns, and $A_i$ identifies the entity for a given row ($A_i$ is the identity column).

An anonymity policy is a function $\alpha:A_i \times C\backslash\{A_i\} \to L$.

Every mapping $(A_i, A_j)$ is assigned a label $l = \alpha(A_i, A_j)$. Mapping $(A_i, A_j)$ can only be revealed to entities that have been granted at least one label $l' \geq l$.

An anonymization policy is a function $\delta: L \to N$, where N is the set of natural numbers. For example, $\delta(\text{secret}_1, \text{public}) = 10$, where number 10 represents 10-anonymity.

Another topic for consideration is aggregation. Consider the confidential mapping of (Employee Name, Salary). If the employee salaries for a department are summed into a total, an anonymity policy can allow the total department salary to be released to certain principals, as long as the department is sufficiently large. Aggregation is a form of obfuscation, in that aggregation is a partitioning into a single equivalence class of indistinguishable values. An aggregation of k values is thus, by definition, k-anonymous.

Now static enforcement of anonymity is described. An information-flow anonymity policy is defined above. Data confidentiality mappings (e.g., confidentiality mappings 220) and k-anonymity requirements with respect to these mappings are used to specify the anonymity policy.

A focus is placed here on a problem of enforcing the anonymity policy for a given program. This entails ensuring that the program code sufficiently obfuscates data before releasing the data at release points.

Figure 7:
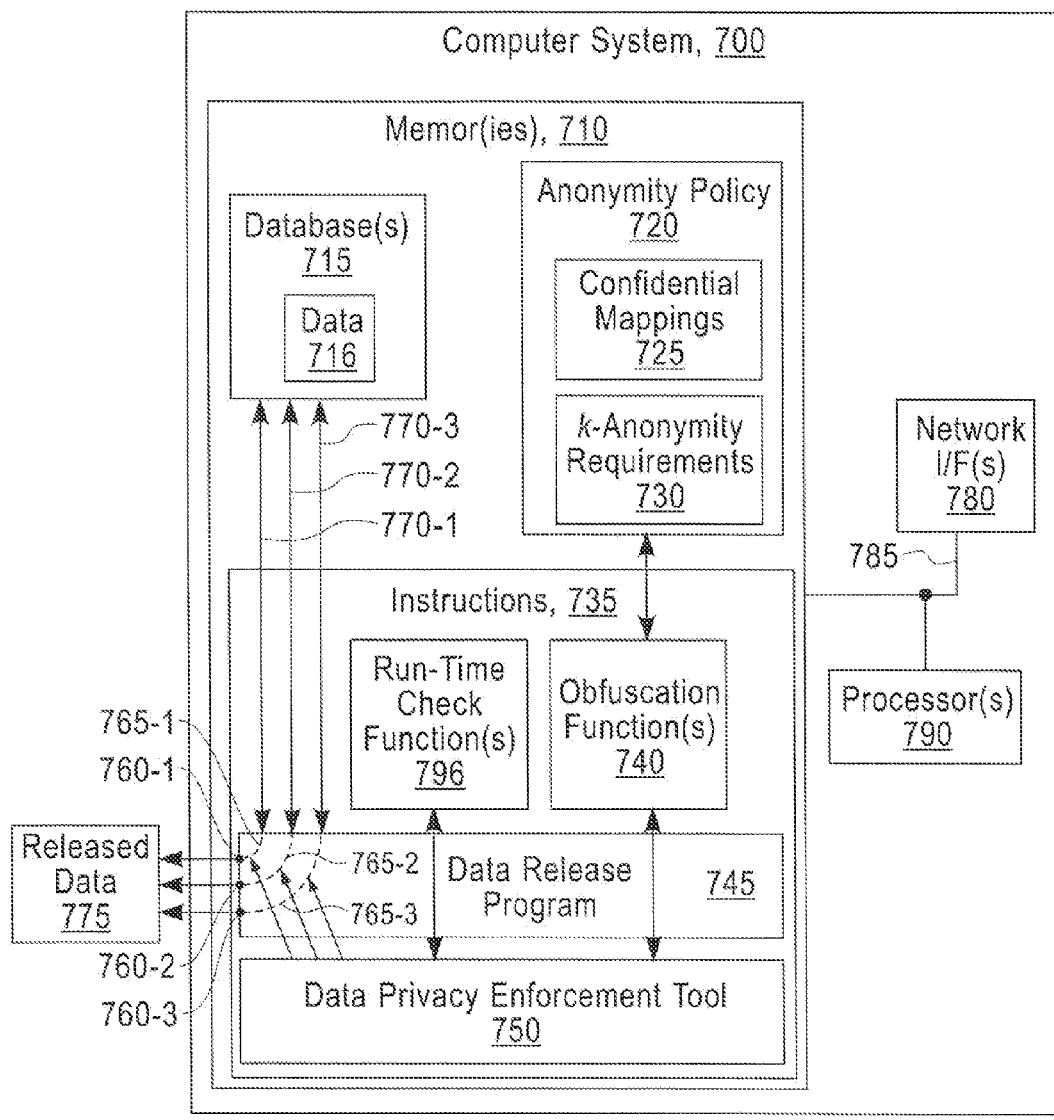
FIG. 7 is block diagram of an exemplary computer system suitable for implementing the invention.

Referring to FIG. 7, this figure is a block diagram of an exemplary computer system suitable for implementing the invention. A computer system 700 includes one or more memories 710, one or more network interfaces 780, and one or more processors 790, operatively coupled together through one or more buses 785. The one or more memories 710 include one or more databases 715, an anonymity policy 720 having confidential mappings 725 (e.g., such as confidential mapping 220 of FIG. 2), and k-anonymity requirements 730. The one or more memories 710 also include instructions 735, which when executed by the one or more processors 790 make the computer system 700 perform actions. The instructions 735 include one or more obfuscation functions 740, a data release program 745 and a data privacy enforcement tool 750. The data privacy enforcement tool 750 contains instructions that cause the computer system 700 to perform one or more of the actions described herein. The one or more databases 715 contain data 716 (e.g., as shown in FIGS. 2-6 and 13).

The data release program 745 is any program that will query (e.g., via queries 770-1 through 770-3) the one or more databases 715 and release data as released data 775. Such released data 775 might be released publicly or released to principals having low integrity. The data is released at release points 760, of which three, 760-1 through 760-3, are shown. The data privacy enforcement tool 750 ensures that obfuscation functions 740 are used in the paths 765-1 through 765-3 from a respective query 770-1 through 770-3 to respective release points 760-1 through 760-3, when such functions are necessary (as described in more detail below). It should be noted that there could be multiple release points 760 and multiple paths 756 for single queries 770, or there could be multiple queries 770 per release point 760.

The obfuscation functions 740 are typically provided by a user. The obfuscation functions 740 should meet the anonymity policy 720 (e.g., the function $\alpha:A_i \times C\backslash\{A_i\} \to L$, described above, or a representation thereof). As described above, the anonymity policy 720 takes into account the confidential mappings 725 (e.g., confidential mapping 220 of FIG. 2 or the mapping $(A_i, A_j)$ described above, or a representation thereof), and defines the k-anonymity requirements 730. In the example of FIGS. 5 and 6, the k-anonymity requirement was two.

The run-time check function(s) 796 are generated in certain exemplary embodiments herein, as described below. Additionally, the run-time check function(s) 796 may also include obfuscation function(s) 740.

It is noted that the anonymity policy 720 is shown as data within the one or more memories 710, but the policy 720 may also be part of the data privacy enforcement tool 750. Similarly, the obfuscation functions 740 are shown separately from the data privacy enforcement tool 750, but may be part of the data privacy enforcement tool 750.

Figure 8:
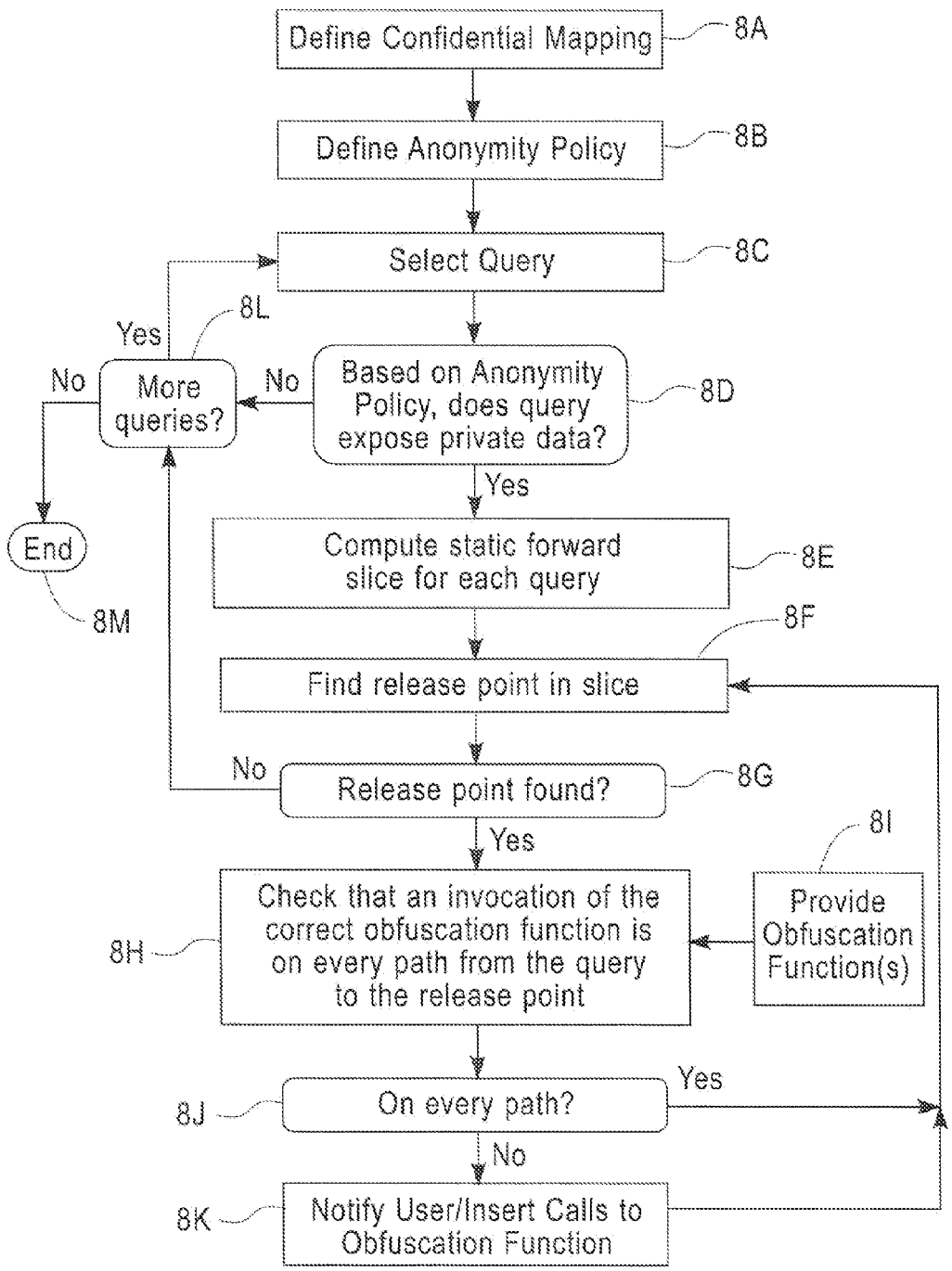
FIG. 8 is a block diagram of an exemplary flowchart for providing enforcement of data privacy to maintain obfuscation of certain data.
Figure 9A:
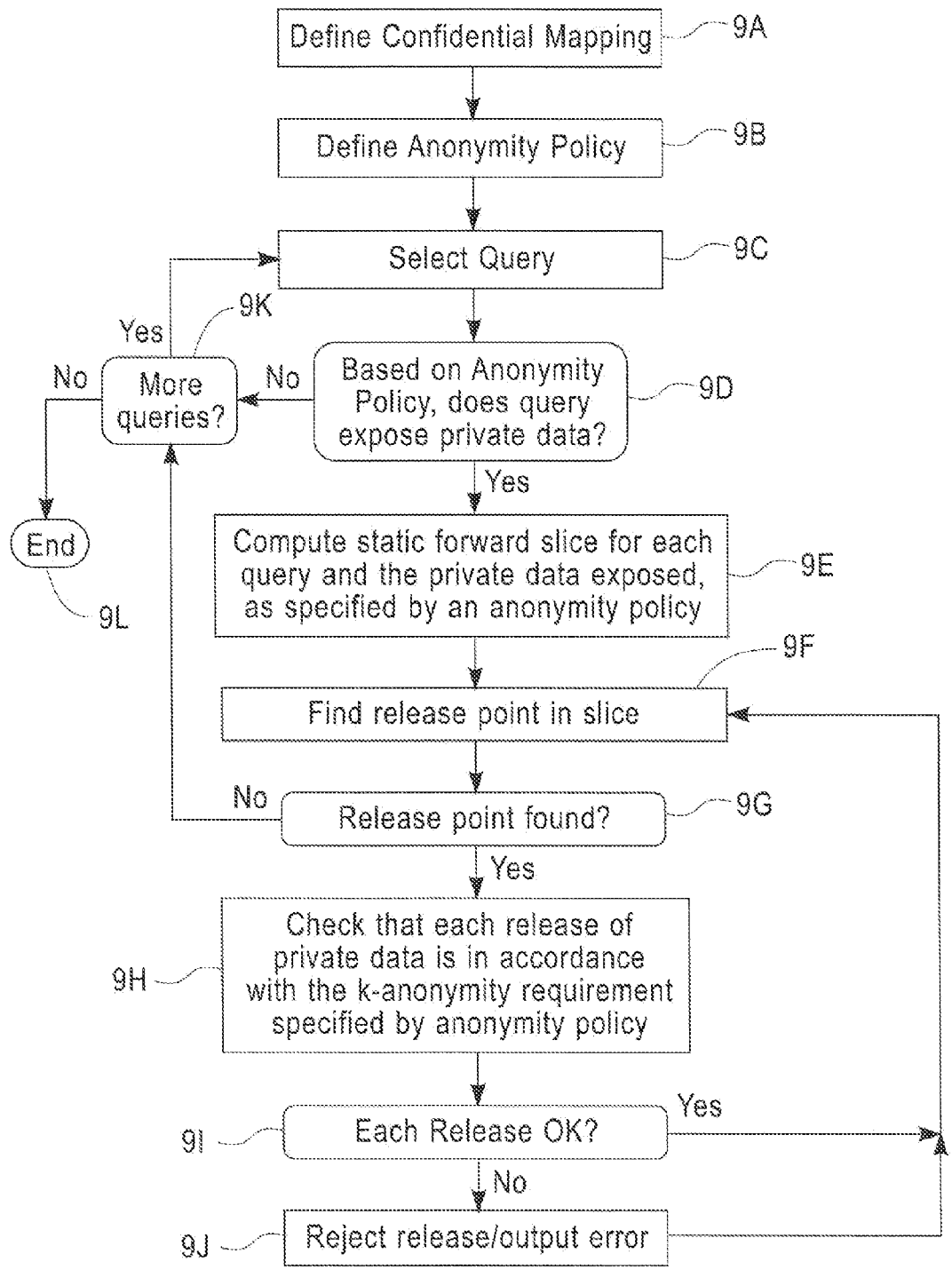
FIG. 9A is a block diagram of another exemplary flowchart for providing enforcement of data privacy to maintain obfuscation of certain data.
Figure 9B:
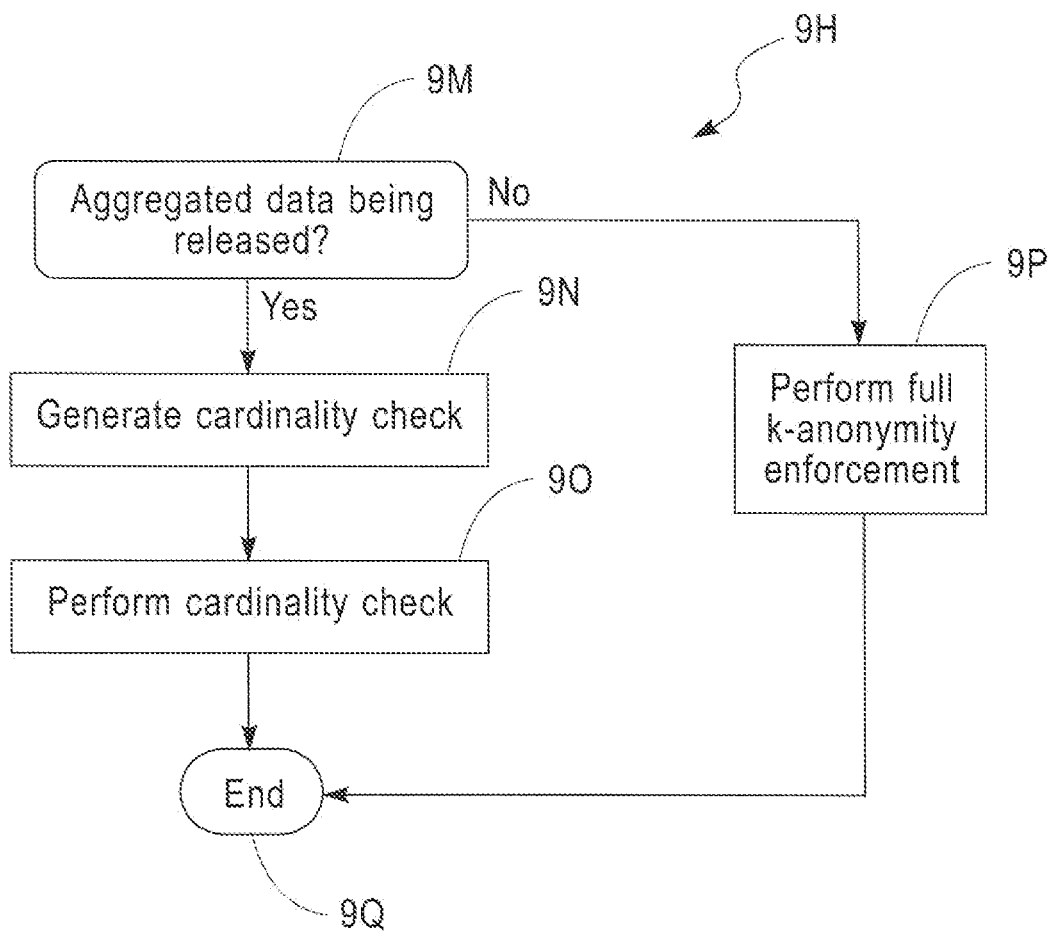
FIG. 9B is a block diagram of how on block in FIG. 9A might be performed in an exemplary embodiment.

FIG. 7 is now described in more detail in reference to FIGS. 8, 9A, and 9B. It is noted that most of the blocks in FIGS. 8, 9A, and 9B would be performed by the data privacy enforcement tool 750. One technique for statically enforcing an anonymity policy is to determine that no release point 760 exposes private data 716 unless sufficiently obfuscated in accordance with the policy 720. Two approaches for such a static mechanism are now considered.

The first approach is described in reference to FIGS. 7 and 8 (and previous figures as required). FIG. 8 shows a block diagram of an exemplary flowchart of a method for providing enforcement of data privacy to maintain obfuscation of certain data and for implementing the first approach. A user defines confidential mappings 725 in block 8A and defines the anonymity policy 720 in block 8B. It is noted that defining the anonymity policy 720 includes defining the k-anonymity requirement 730.

In broad terms, in this first approach, the user provides, as an input to data privacy enforcement tool 750, the obfuscation function 740 specific to each database query 770 that returns values (of data 715) from sensitive columns (i.e., those columns associated with confidential mappings 725). The user inserts calls in the data release program 745 to obfuscation functions 740 as needed and as directed to by the data privacy enforcement tool 750. Alternatively, the data privacy enforcement tool 750 could insert calls to the obfuscation functions 740.

In this case, the static analysis verifies that the correct obfuscation function is invoked along every path from the query to a release point. This analysis guarantees that the output produced by each release point 760 has been obfuscated by the required function 740.

In more specific terms, a query is selected in block 8C. Based on the anonymity policy 720 (e.g., particularly the confidential mappings 725), the data privacy enforcement tool 750 determines whether the query exposes private data in block 8D. If not (block 8D=NO), the method proceeds to block 8L. If so (block 8D=YES), the method proceeds to block 8E.

More precisely, the static analysis performs the following:
Compute the static forward slice with respect to each query 770 and the private data 716 that the query 770 exposes, as specified by the anonymity policy 720. In other words, the confidential mappings 725 define which columns of data in the database 715 are private data subject to k-anonymity requirements 730. The computation occurs in block 8E.

In block 8F, a release point 760 is attempted to be found in the slice. If a release point 760 is found in the data release program 745 (block 8G=YES), it is checked that an invocation of the correct obfuscation function 740 is on every path 765 from the query 770 (e.g., a source) to the release point 760 (e.g., a sink). This occurs in block 8H. It is typically at this point that the user provides the obfuscation function(s) 740 in block 8I for the particular query 770. However, the user could provide all such obfuscation functions 740 at a different point. If any path 65 does not have an invocation of the correct obfuscation function 740 (block 8J=NO), then in block 8K the user is notified to insert a call to an obfuscation function 740 or the data privacy enforcement tool 750 inserts a call to the obfuscation function 740. If an invocation is found on every path 755 (block 8J=YES), the method continues in block 8F.

If no release point is found (block 8G=NO), the method continues in block 8L, where it is determined if more queries still in the data release program 765. If there are no more queries 770 (block 8L=No), then the method ends in block 8M; otherwise, block 8C is performed again.

The role of a query-specific obfuscation function 740 is to anonymize data returned by the query in accordance with the anonymity policy 720. Where k-anonymity 730 is required, the obfuscation techniques described above, e.g., partitioning and aggregation, can be used to satisfy the required anonymity. The analysis does not check the correctness of the user-written obfuscation functions 740.

In general, in the presence of multiple dynamically constructed queries, static confirmation that the correct anonymization function is being always possible. In these cases, metadata should be used to provide necessary hints to the analyzer.

A second approach is automatic generation of run-time checks, which is illustrated by, e.g., FIGS. 7, 9A, and 9B. In general, at every release point 760, the static analysis (e.g., by tool 750) generates the required run-time check function 796 to ensure that the anonymity policy is not violated. The run-time check function 796 may include a discrete obfuscation function 740. The tool enforces k-anonymity by statically generating the run-time check of whether the released data is k-anonymous.

An observation is that a cardinality check for size greater than or equal to k is sufficient to enforce k-anonymity for aggregated data. This is illustrated in an example below. In the general case, a run-time inspection of the data 716, to determine its level of anonymity, may be required.

A user defines confidential mappings 725 in block 9A and defines the anonymity policy 720 in block 89B. It is noted that defining the anonymity policy 720 includes defining the k-anonymity requirement 730.

In block 9C, a query is selected. It is determined in block 9D whether the query 770 exposes private data (e.g., by determining whether the query accesses a column associated with a confidential mapping 725). If the query 770 does not expose private data (block 9D=NO), the method proceeds to block 9K. If the query 770 does expose private data (block 9D=YES), the method proceeds to block 9E.

Statically generating the required run-time check requires a static analysis, again based on forward slicing with respect to database queries 770. More precisely, the static analysis performs the following.

The static analysis computes the static forward slice with respect to each query 770 and the private data 716 that the query 770 exposes, as specified by the anonymity policy 720. In other words, the confidential mappings 725 define which columns of data in the database 715 are private data subject to k-anonymity requirements 730. The analysis occurs in block 9E.

For each release point 760 in the forward slice, check each release of private data is in accordance with the k-anonymity requirement 730 specified by the anonymity policy 720. This is performed by finding any release points in the slice (block 9F), and if a release point is found (block 9G=YES), checking to ensure that each release (at a release point 760) of private data 716 is in accordance with the k-anonymity requirement 730 specified by the anonymity policy 720. The check occurs in block 9H. If each release in the slice is not in accordance with the requirement (block 9I=NO), the release is rejected and potentially an error is output (block 9J). If each release in the slice is in accord with the requirement (block 9I=YES), the method transitions to block 9F.

It is noted that block 9H may be performed as shown in FIG. 9B. In the case of aggregated data (block 9M=YES), the required cardinality check is generated (block 9N) and is performed (block 9O). The slicing analysis should be augmented to include the recognition of aggregated private data 716 in this case. The static analysis performed in Michael Burke, Igor Peshansky, Mukund Raghavachari, and Christoph Reichenbach, "Analysis of imperative xml programs", in DBPL 2007: 11th International Symposium on Database Programming Languages, 2007, recognizes aggregations of XML nodes into sets that represent symbolic XPath expressions. A similar analysis may be used here. If aggregated data 716 is not being released (block 9M=NO), then a full k-anonymity enforcement is performed in block 9P. In block 9Q, this portion of the method ends and operation transitions to block 9I of FIG. 9A).

If there are no release points found in the current slice (block 9G=NO), the method continues in block 9K. If there are more queries 770 found as the data release program 745 executes (block 9K=YES), the method continues in block 9C. If no more queries 770 are found (block 9K=NO), the method ends in block 9L.

One possible suitable static forward slicing analysis is described in Frank Tip, "A survey of program slicing techniques," Journal of Programming Languages, 3(3):121-189, 1995. This analysis computes the set of statements potentially affected by the values returned by an SQL API (such as JDBC) query that reads values from specified database columns. A slicing criterion is specified by a pair (program point, set of variables), were the set of variables is a subset the set of program variables. In an exemplary embodiment of the instant case, the program point is a Java database connectivity (JDBC) is other structured query language (SQL) application programmer interface (API) query method invocation; the data component of the criterion is the set of values returned from specified columns (i.e., the columns having confidential mappings 725). This is an extension of a traditional slicing framework in that the set of values is not part of the program state: the values are not held in program variables. They instead are part of an external state, the relational table, such as the one shown in FIG. 4.

One possible slicing analysis follows thin slicing in not including control dependences in the computation. Such thin slicing is described in Manu Sridharan, Stephen J. Fink, and Rastislav Bodik, "Thin slicing," in PLDI 2007: Proceedings of the ACM SIGPLAN 2007 Conference on Programming Language Design and Implementation, pages 112-122, 2007.

To further refine the slicing analysis, properties of the SQL API are provided as input to the slicing analysis. These include properties associated with the SQL. API methods. An "occuous" API method call is one that has an effect, dependent on the column data, on some externally visible state. Examples of such an effect include returning values in a column, writing them to the heap, externally outputting them, and storing them in a database. If for any invocation of a method, it is not occuous, that method has the property of being "innocuous." For example, in JDBC, where "rs" has type ResultSet and "select" has type Statement, the methods rs.close( ), rs.next( ), and select.close( ) are all innocuous. A method invocation of an innocuous method can always be excluded from a slice.

For a more detailed description of a suitable forward slicing analysis, see Michael C. Burke, Rosalva E. Gallardo-Valencia, and Igor Peshansky, "Impact analysis of object-oriented source code with respect to database schema modifications," Technical Report RC24703, IBM Watson Research Center, 2008.

Now that certain exemplary embodiments of the invention have been described, some examples in presented. The first example concerns an employee database. Consider a database 715 in which each employee has a record with fields: name, department, date of birth, date of hire, and salary. The (name, salary) mapping is confidential. The total salary in a department is not secret, if the size of the department is sufficiently large. Thus salary information is anonymized with respect to a size parameter k. The value of k can be derived from a formula specified by the database administrator. For example, where the policy of the company is that an individual annual salary is to be privatized within a certain range (perhaps 10,000 dollars), then k can be calculated from a formula based on that constraint and information available to unauthorized users, such as the minimum and maximum salaries for a given position.

Consider the fragment of JDBC code in FIG. 10, which displays the total salary of a department. The print statement is a release point 760 and a possible breakage of k-anonymity. Thus the print statement needs to be preceded by a cardinality check of getEmployees.

An active attacker can write a program that compares the total salary of a department before and after the addition of new employees. If the number of new employees in the department is less than k, then the salary of fewer than k employees can be inferred, violating the anonymity policy. Consider the code fragment in FIG. 11.

The code contains three print (release point 760) statements. As in the previous code example, the first print statement can possibly break k-anonymity, and needs to be preceded by a cardinality check. In the second print statement, no confidential data or mapping is displayed, so no check is needed. The final print statement can possibly break k-anonymity through a comparison, and needs to be preceded by a check of the cardinality of dept_newsalary-dept_salary.

This cardinality check ensures that the information is displayed only if k or more new employees have been added to the department, preserving the anonymity policy against a potential active attack.

This example illustrates that aggregation is a form of obfuscation, where an anonymity policy as always requires a degree of obfuscation. As observed in above, a cardinality check for size>=k is sufficient to enforce k-anonymity for aggregated data.

An example for an online bookstore is now described. An online bookstore can generate a table in which every purchase is an entry that includes the name of the buyer, gender, zip code, age, and the purchased book. FIG. 12 is an example of an entry used for a bookstore. The web site wants to provide information to users such as: "Users who bought book A also bought book B." FIG. 13 is an example of a table of entries for purchases made at the bookstore.

The program code in FIG. 14A generates the list of users who bought the book ABC. FIG. 14B is a list output by the program code of the users that bought book ABC.

Figure 15B:
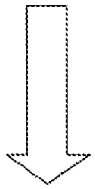
FIG. 15B shows an example of results of a query of what other male users in a certain age range and in a certain area who bought book ABC also bought books and results of the query of what other male users in a certain age range and in a certain area who bought book ABC also bought book XYZ.

A more specific report can be generated by the code in FIG. 15A, which shows a query from FIG. 14A being modified. FIG. 15B shows an example of results of a query of what other male users in a certain age range and in a certain area who bought book ABC also bought books and results of the query of what other mate users in a certain age range and in a certain area who bought book ABC also bought book. XYZ. Additionally, FIG. 15B shows what books other than ABC the users bought. The set of users generated by this code can be combined with the table generated by the above booksToQuantities method to inform a user in this age range and neighborhood that "Other male users in your age range and in your area who bought book ABC also bought book XYZ." An attacker can infer the "age range" and "area" by assuming multiple user identifications (ids) and making small incremental changes to age and zip code. Given knowledge of the age range and area, the attacker might be able to infer, from public information such as records of voters, that only one person in this area and of this gender is in this age range. The attacker can then infer the identity of a person who purchased this book. If the online book store classifies the (person, book) mapping as confidential, then this is a violation of confidentiality. The program code that outputs this information to the user is a release point and potentially breaks k-anonymity. The release should therefore be preceded by a cardinality check: users.size( )>k.

This is an example of a passive attack, where a user who has no write (or read) access to the code can nonetheless access confidential information by assuming multiple identities and posing a sequence of implicit queries.

Another example is shown in FIGS. 16A and 16B. FIG. 16A shows the program code of FIG. 14A modified for a more specific query of what other female users in a certain age range and in a certain area who bought book ABC also bought book XYZ. FIG. 16B shows results of the query of what other female users in a certain age range and in a certain area who bought book ABC also bought book XYZ, how release of this data does not maintain obfuscation, and how multiple attacks can be used to reveal private information. Again, the "age range" and "area" can be inferred by running multiple queries. Furthermore, in this case, there is only a single other female user in a certain age range and in a certain area who bought both books ABC and XYZ. This is 1-anonymity (one-anonymity) and should break k-anonymity and therefore should be proceeded by a cardinality check of users.size( )>k.

Figure 17:
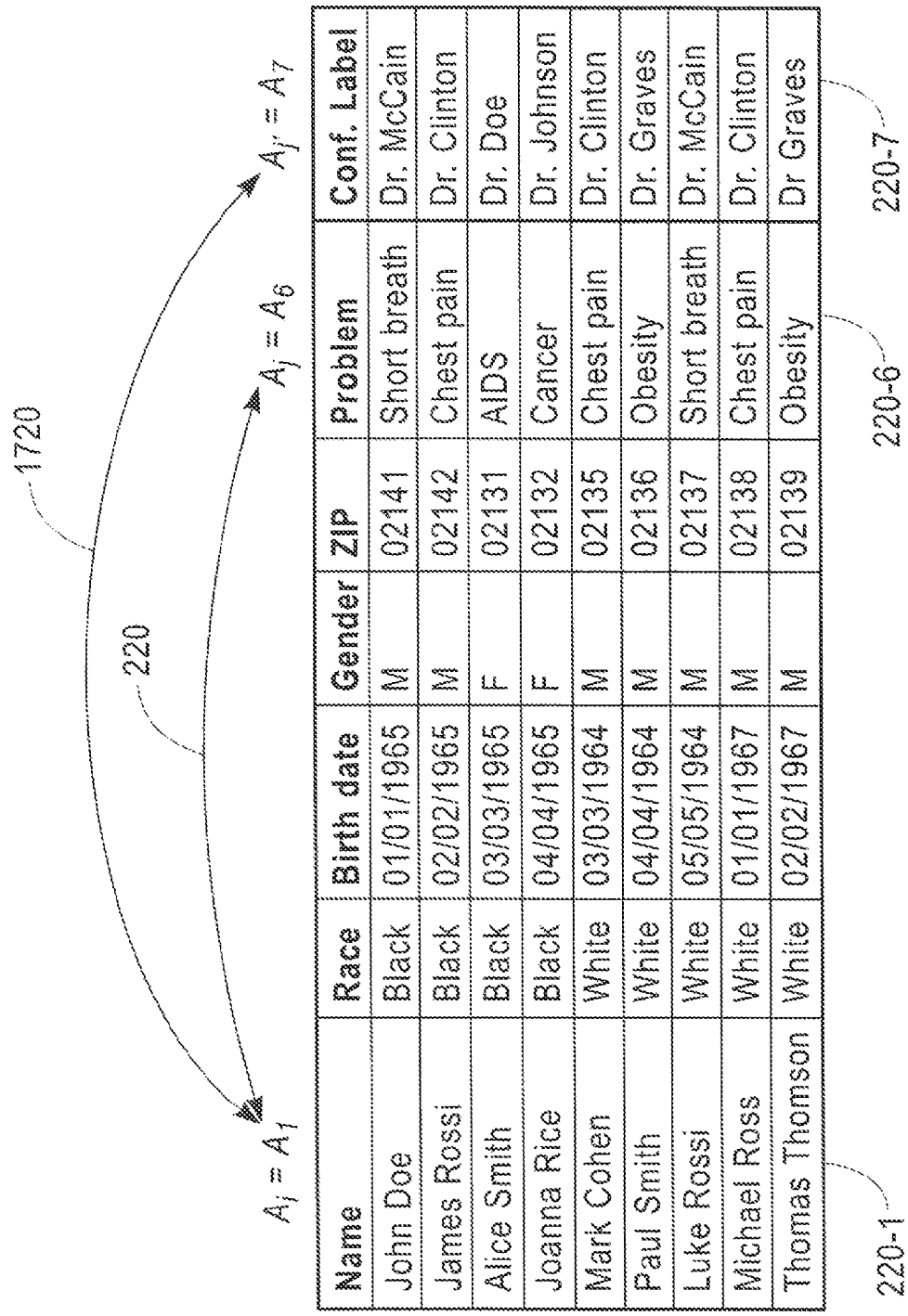
FIG. 17 is an example of the private medical database table of FIG. 2, with an extra column and multiple confidential mappings.

One last example is shown in FIG. 17. FIG. 17 is an example of the private medical database table of FIG. 2, with an extra column 220-7 and multiple confidential mappings. The confidentiality policy on the medical record for Alice Smith is Dr. Doe. Dr. Doe is a human immunodeficiency virus (HIV) specialist. Even without looking at the medical record for Alice Smith, an attacker can inter that Alice Smith has acquired immunodeficiency syndrome (AIDS). For this reason, there are two confidential mappings 210 and 1720. Thus, k-anonymity will also be applied to the data in column 220-7. This figure therefore shows how anonymizing confidentiality mappings with the techniques presented above can also be used to anonymize confidentiality policies, which is a very important feature of this invention since a confidentiality policy can be more confidential than the confidential data itself.

It should be noted that although "columns" of databases have been discussed herein, the invention is not restricted to such columns and can be applied to any sets of data.

As should be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer-readable medium(s) having computer-readable program code embodied thereon.

Any combination of one or more computer-readable medium(s) may be utilized. The computer-readable medium may be a computer-readable signal medium or a computer-readable storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain, or store a program for use by or in connection with an instruction execution system, apparatus, or device.

A computer-readable signal medium ma include a propagated data signal with computer-readable program code embodied therein, for example, in baseband or as part of a carrier wave. Such a propagated signal may take any of a variety of forms, including, but not limited to, electro-magnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device.

Program code embodied on a computer-readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or assembly language or similar programming languages. Such computer program code may also include code for field-programmable gate arrays, such as VHDL (Very-high-speed integrated circuit Hardware Description Language).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer, other programmable data processing apparatus, or other devices to function in a particular manner, such that the instructions stored in the computer-readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The foregoing description has provided by way of exemplary and non-limiting examples a full and informative description of the best techniques presently contemplated by the inventors for carrying out embodiments of the invention. However, various modifications and adaptations may become apparent to those skilled in the relevant arts in view of the foregoing description, when read in conjunction with the accompanying drawings and the appended claims. All such and similar modifications of the teachings of this invention will still fall within the scope of this invention.

Furthermore, some of the features of exemplary embodiments of this invention could be used to advantage without the corresponding use of other features. As such, the foregoing description should be considered as merely illustrative of the principles of embodiments of the present invention, and not in limitation thereof.

What is claimed is:

1. A method, comprising:
    determining, by a microprocessor, whether data to be released from a database maps to at least one confidential mapping between sets of data in the database; and
    in response to the data mapping to the at least one confidential mapping, determining whether release of the data meets at least one predetermined anonymity requirement of an anonymity policy, wherein determining whether release of the data meets at least one predetermined anonymity requirement of an anonymity policy further comprises performing static enforcement of the anonymity policy by analyzing program code without executing the program code, wherein the program code performs release of the data at one or more release points when the program code is executed, and wherein determining whether release of the data meets at least one predetermined anonymity requirement of an anonymity policy and performing static enforcement of the anonymity policy further comprises:
  determining, during the static enforcement whether an invocation of an obfuscation function is performed in the program code on at least one path from a query to at least one of the one or more release points at which the data would be released by the program code when the program code is executed; and
  in response to an invocation of the obfuscation function not being performed in the program code on the at least the path from the query to the at least one release point at which the data would be released by the program code, performing during the static enforcement at least one action.

2. The method of claim 1, wherein determining whether an invocation of an obfuscation function is performed further comprises determining whether an invocation of an obfuscation function is performed in the program code on every one of the at least one paths from the query to the at least one release points at which the data would be released.

3. The method of claim 1, further comprising receiving an obfuscation function from a user and wherein performing at least one action comprises inserting during the static enforcement and in the program code a call to the received obfuscation function, the call inserted in the at least one path from the query to the at least one release point at which the data would be released by the program code.

4. The method of claim 1, wherein performing the at least one action comprises notifying a user of lack of invocation of an obfuscation function on the at least one path.

5. The method of claim 1, wherein performing the at least one action comprises inserting a call to an obfuscation function in the program code in one or more of the at least one paths.

6. The method of claim 1, wherein each of the sets corresponds to a column of the database.

7. An apparatus, comprising:
  at least one processor; and
  at least one memory including instructions,
  the at least one processor configured, in response to executing the instructions, to cause the apparatus to perform at least the following:
  determining whether data to be released from a database maps to at least one confidential mapping between sets of data in the database; and
  in response to the data mapping to the at least one confidential mapping, determining whether release of the data meets at least one predetermined anonymity requirement of an anonymity policy, wherein determining whether release of the data meets at least one predetermined anonymity requirement of an anonymity policy further comprises performing static enforcement of the anonymity policy by analyzing program code without executing the program code, wherein the program code performs release of the data at one or more release points when the program code is executed, and wherein determining whether release of the data meets at least one predetermined anonymity requirement of an anonymity policy and performing static enforcement of the anonymity policy further comprises:
  determining the one or more release points in the program code; and
  determining, during the static enforcement, whether the release or the data from the one or more release points is in accordance with a k-anonymity requirement specified by the anonymity policy.

8. The apparatus of claim 7, wherein determining whether the release of the data is in accordance with a k-anonymity requirement specified by the anonymity policy and performing static enforcement of the anonymity policy further comprises generating, during the static enforcement, a check function that determines whether the release of the data would be in accordance with the k-anonymity requirement.

9. The apparatus of claim 7, wherein determining whether the release of the data is in accordance with a k-anonymity requirement specified by the anonymity policy and performing static enforcement of the anonymity policy further comprises generating and performing, during the static enforcement, a cardinality check to ensure cardinality greater than k for at least data to be released in at least one of the sets of data associated with a corresponding at least one confidential mapping.

10. The apparatus of claim 9, wherein the at least one confidential mapping further comprises a plurality of confidential mappings between a plurality of sets of data in the database.

11. A method, comprising:
  determining, by a microprocessor, whether data to be released from a database maps to at least one confidential mapping between sets of data in the database; and
  in response to the data mapping to the at least one confidential mapping, determining whether release of the data meets at least one predetermined anonymity requirement of an anonymity policy, wherein determining whether release of the data meets at least one predetermined anonymity requirement of an anonymity policy further comprises performing static enforcement of the anonymity policy by analyzing program code without executing the program code, wherein the program code performs release of the data at one or more release points when the program code is executed, and wherein determining whether release of the data meets at least one predetermined anonymity requirement of an anonymity policy and performing, static enforcement in the anonymity policy further comprises:
  determining the one or more release points in the program code; and
  determining, during the static enforcement, whether the release of the data from the one or more release points is in accordance with a k-anonymity requirement specified by the anonymity policy.

12. The method of claim 11, wherein determining whether the release of the data is in accordance with a k-anonymity requirement specified by the anonymity policy and performing static enforcement of the anonymity policy farther comprises generating, during the static enforcement, a check function that determines whether the release of the data would be in accordance with the k-anonymity requirement.

13. The method of claim 11, wherein determining whether the release of the data is in accordance with a k-anonymity requirement specified by the anonymity policy and performing static enforcement of the anonymity policy further comprises generating and performing, during the static enforcement, a cardinality check to ensure cardinality greater than k for at least data to be released in at least one of the sets of data associated with a corresponding at least one confidential mapping.

14. The method of claim 11, wherein the at least one confidential mapping further comprises a plurality of confidential mappings between a plurality of sets of data in the database.

\* \* \* \* \*